United States Patent
Li

(10) Patent No.: US 6,569,489 B1
(45) Date of Patent: May 27, 2003

(54) BIOACTIVE CERAMIC COATING AND METHOD

(75) Inventor: Panjian Li, Mansfield, MA (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/574,358

(22) Filed: May 19, 2000

Related U.S. Application Data

(63) Continuation-in-part of application No. 09/038,444, filed on Mar. 11, 1998, now Pat. No. 6,139,585.

(51) Int. Cl.$^7$ .......................... A61L 27/00; A61K 27/00; B05D 3/12
(52) U.S. Cl. .................. 427/2.26; 427/2.24; 427/2.27; 427/435; 427/443.2
(58) Field of Search .................... 427/2.26, 2.27, 427/435, 443.2, 2.24

(56) References Cited

U.S. PATENT DOCUMENTS

| | | | |
|---|---|---|---|
| 4,285,223 A | 8/1981 | Das et al. .................... 72/42 |
| 5,178,845 A | 1/1993 | Constantz et al. .......... 423/305 |
| 5,188,670 A | 2/1993 | Constantz ................... 118/667 |
| 5,205,921 A | 4/1993 | Shirkanzadeh ............. 205/318 |
| 5,231,169 A | 7/1993 | Constantz et al. .......... 530/356 |
| 5,279,831 A | 1/1994 | Constantz et al. .......... 424/423 |
| 5,336,264 A | 8/1994 | Constantz et al. ............ 623/16 |
| 5,397,362 A | 3/1995 | Noda ........................... 623/16 |
| 5,441,536 A | 8/1995 | Aoki et al. ................. 427/2.27 |
| 5,455,231 A | 10/1995 | Constantz et al. ............ 514/21 |
| 5,496,399 A | 3/1996 | Ison et al. .................... 106/35 |
| 5,545,226 A | 8/1996 | Wingo et al. ................. 623/16 |
| 5,569,442 A | 10/1996 | Fulmer et al. .............. 423/311 |
| 5,571,493 A | 11/1996 | Fulmer et al. .............. 423/308 |
| 5,580,623 A | 12/1996 | Fulmer et al. ............. 428/34.1 |
| 5,612,049 A | 3/1997 | Li et al. ...................... 424/422 |
| 5,683,461 A | 11/1997 | Lee et al. ..................... 623/16 |
| 5,683,496 A | 11/1997 | Ison et al. .................... 106/35 |
| 5,683,667 A | 11/1997 | Fulmer et al. .............. 423/311 |
| 5,697,981 A | 12/1997 | Ison et al. .................... 623/16 |
| 5,728,395 A | 3/1998 | Ohtsuka et al. ............. 424/422 |
| 5,759,376 A | 6/1998 | Teller et al. .................. 205/50 |
| 5,817,326 A | 10/1998 | Nastasi et al. .............. 424/426 |
| 5,820,632 A | 10/1998 | Constantz et al. ............ 623/16 |
| 5,824,087 A | 10/1998 | Aspden et al. ................ 623/16 |
| 5,868,796 A | 2/1999 | Buechel et al. ............... 623/16 |
| 5,900,254 A | 5/1999 | Constantz .................... 424/602 |
| 5,958,430 A | 9/1999 | Campbell et al. ........... 424/400 |
| 5,958,504 A | 9/1999 | Lee et al. ................... 427/2.24 |
| 6,136,369 A | * 10/2000 | Leitao et al. ............... 427/2.26 |
| 6,207,218 B1 | * 3/2001 | Layrolle et al. ........... 427/2.24 |

FOREIGN PATENT DOCUMENTS

| | | | |
|---|---|---|---|
| EP | 0 389 713 A1 | 10/1990 | ......... A61L/27/00 |
| EP | 0 437 975 A1 | 7/1991 | ......... A61L/27/00 |
| JP | 8 40711 | 2/1996 | ......... A61L/27/00 |
| WO | WO 97/41273 | 11/1997 | ............ C23C/4/18 |
| WO | WO 98/28025 | 7/1998 | ......... A61L/27/00 |

OTHER PUBLICATIONS

B.C. Bunker, et al., "Ceramic Thin–Film Formation on Functionalized Interfaces Through Biomimetic Processing", *Science*, The American Association for the Advancement of Science, vol. 264, Apr. 1, 1994, pp. 48–55.

* cited by examiner

*Primary Examiner*—Shrive P. Beck
*Assistant Examiner*—Jennifer Kolb Michener
(74) *Attorney, Agent, or Firm*—Nutter McClennen & Fish LLP

(57) ABSTRACT

A bioactive bone mineral carbonated nano-crystalline apatite is chemically bonded to a variety of substrates, including implantable prostheses. This coating is applied uniformly to substrate surfaces of varying geometry and surface textures. It is firmly secured to the substrate and encourages rapid and effective bone ingrowth. The coating is applied by immersing the substrate in an aqueous solution containing calcium, phosphate and carbonate ions. Other ions, such as sodium, potassium, magnesium, chloride, sulfate, and silicate, may optionally be present in the solution. The solution is exposed in a controlled environment when it reacts with the substrate to form the coating.

14 Claims, 10 Drawing Sheets

MAGNIFICATION: 500x

MAGNIFICATION: 250x

MAGNIFICATION: 1000x

BIOACTIVE CERAMIC COATING AND METHOD

CROSS-REFERENCE TO RELATED APPLICATIONS

This application is a Continuation-in-Part of and claims priority to U.S. Ser. No. 09/038,444, filed on Mar. 11, 1998 now U.S. Pat. No. 6,139,585. The contents of the aforementioned application are hereby incorporated by reference.

BACKGROUND OF THE INVENTION

The invention relates to bioimplantable articles having a bioactive ceramic coating, which reassembles bone mineral, and to methods for forming such coating on implantable articles.

It is desirable to apply mineralized and/or ceramic coatings to a variety of articles. Biological implants including joint prostheses and dental implants represent one class of articles to which such coatings are frequently applied. The substrate to which these coatings is applied is usually a metal or a plastic, but the coatings can be applied to other substrates such as ceramic and silicon.

Biological implants, such as joint and dental prostheses, usually must be permanently affixed or anchored within bone. In some instances it is acceptable to use a bone cement to affix the prosthesis within bone. In the case of many joint prostheses, however, it is now more common to affix the joint prosthesis by encouraging natural bone ingrowth in and around the prosthesis. Bone-to-implant interfaces that result from natural bone ingrowth tend to be stronger over time and more permanent than are bone cement-prosthesis bonds.

Optimal bone ingrowth requires that natural bone grow into and around the prosthesis to be implanted. Bone ingrowth and prosthesis fixation can be enhanced by providing irregular beaded or porous surfaces on the implant. Although various materials, including titanium alloys, are biocompatible, they are not necessarily bioactive because they can neither conduct bone formation nor form chemical bonds with bone.

Thus, enhanced fixation of implants within bone can be attained by coating the implant with a bioactive mineralized and/or ceramic material. Such coatings have be shown to encourage more rapid bone ingrowth in and around the prosthesis.

Various techniques are used to apply mineralized and/or ceramic coatings to bioimplantable substrates. These coatings are typically made of ceramics and tend to be characterized by a relatively large crystal size. These coatings can be applied by a variety of techniques including plasma spraying, ion implantation, and sol-gel processing. These coating methods, although relatively widely used, do have some drawbacks. For example, the applied coatings tend to possess micropores and macropores and they can be relatively thick and brittle. These coatings can also possess chemical defects, and they do not always adhere well to substrates. Finally, such coatings are not evenly and uniformly applied to surfaces with complex geometries, such as porous surfaces with undercut regions.

It has been well documented that calcium phosphate ceramics, especially hydroxyapatite, can conduct bone formation. Hydroxyapatite ceramic has been successfully applied as a coating on cementless metallic implants to achieve quick and strong fixation. Thermal plasma spraying is one of the more common methods used to produce hydroxyapatite coatings. However, the resulting plasma-sprayed hydroxyapatite coating is of relatively low density and is not uniform in structure or composition. The adhesion between the coating and substrate is generally not very strong, especially after long term exposure within the body. The generation of hard ceramic particles, resulting from the degradation of thermal plasma sprayed coating, and coating delamination, are major concerns.

Low temperature processes have also been implemented to produce hydroxyapatite ceramic coatings using water-based solutions. Since aqueous solutions can reach any open space, these low-temperature processes can be efficiently used in the case of substrates with complex surface geometries. The hydroxyapatite coating that is formed from this solution can be more biologically friendly to bone tissue than is the plasma-sprayed hydroxyapatite coating which is produced by a high temperature process. However, currently known low temperature processes typically require pretreatment of the substrate.

The calcium phosphate ceramic made of hydroxyapatite [HA, $Ca_{10}(PO_4)_6(OH)_2$] has been demonstrated to be capable of inducing bone formation and bonding to bone. Because of this osteoconductive property, HA ceramic has been used in repair of bone defects. Metallic implants are often coated with HA ceramic to allow a rapid bond apposition and thereby to entail fixation of the implants in bone without use of bone cement.

One example of an aqueous system-based coating technique is disclosed in U.S. Pat. No. 5,205,921 in which bioactive ceramic coatings are electrodeposited upon a substrate. Bunker et al., *Science* 264, 48–55 (1994) disclose a technique for applying an octacalcium phosphate upon a substrate by immersing the substrate in a solution containing calcium chloride after surface treating the substrate with a material such as chlorosilane. Other techniques, such as disclosed in Japanese Patent Application No. 8-40711, form a hydroxyapatite coating by exposing the substrate to calcium phosphate in a pressure reactor. U.S. Pat. No. 5,188,670 discloses a technique for forming a hydroxyapatite coating on a substrate by directing a stream of liquid containing hydroxyapatite particles to apply a fibrous, crystalline coating of hydroxyapatite.

Bone mineral is a calcium phosphate with apatite structure. Bone apatite contains hydrogenophosphate ($HPO_4^{2-}$) ions, carbonate ($CO_3^{2-}$) ions, magnesium ($Mg^{2+}$) ions, sodium ($Na^+$) ions and other trace ions, with sodium and magnesium ions substituting for a percentage of calcium ions in the apatite structure and with carbonate ions substituting for $PO_4^{3-}$ and $OH^-$ in hydroxyapatite.

Chemically absorbed water is found in bone apatite. In addition to these chemical features, bone apatite is generally found in the form of nanocrystals which are poorly crystallized as seen in X-ray diffraction patterns. Bone apatite typically is formed from a physiological solution, namely blood plasma at body temperature in a process called bone mineralization. The organic matrix synthesized by bone cells plays a crucial role in initiating bone apatite formation.

Although HA and bone apatite belong to the same apatite family, they are different. HA ceramic in use today is different from bone apatite in terms of composition, structure and the way they are formed. For example HA contains hydroxyl groups whereas bone apatite does not include hydroxyl functionality or is essentially devoid of hydroxyl functionality, e.g., the hydroxyl content is below current methods of analytical detection. In contrast to hydroxyapatite, bone apatites generally include water molecules within the crystal structure. Furthermore, plasma-sprayed HA coatings are very different from bone mineral apatite, possessing various calcium phosphate salts.

Despite the existence of ceramic coatings and various processes for producing such coatings, there remains a need for improved and reliable processes used to apply bioactive ceramic coatings to substrates.

SUMMARY OF THE INVENTION

The invention provides a dense, substantially pure ceramic coating with a crystal size of less than 1 micrometer. The coating forms a good chemical bond to substrates to which it is applied. Preferably, the coating is a bioactive ceramic coating in the form of a bone mineral carbonated nano-crystalline apatite with chemically adsorbed water having a crystal size of less than about 1 micrometer. The coating contains calcium, magnesium, carbonate and phosphate. Optionally, the coating also includes ions or ionic groups selected from the group consisting of sodium, chlorine, sulfates, silicate and mixtures thereof. Preferably, the ratio of carbonate groups to phosphate groups in the coating is in the range of about 1:100 to 1:3. Further, the atomic ratio of magnesium to calcium is in the range of about 1:100 to 1:4.

One aspect of the present invention is to provide a medical implant with a thin film of a synthetic apatite that is equivalent to, or substantially equivalent to naturally occurring bone apatite composition and its structure. The synthetic apatite film is formed by an soaking implant in an aqueous solution containing calcium, phosphate and bicarbonate ions which allows the apatite to grow on the surfaces of the implants in a crystalline state, i.e., not amorphous. Interaction of bicarbonate ions with the atmosphere above the solution raises the pH of the solution to a pH range of from about 6.5 to about 7.5 as is required for the growth of the synthetic bone apatite film. The synthetic bone apatite film produced by this process, results in an effective bone composition that promotes bone ingrowth and thereby provides implants with bone-bonding properties. The synthetic apatite film can also be used to attract biological molecules such as growth factors for further improvement of bone growth.

The coating can be applied to a variety of substrates, including silicon, metals, ceramics, and polymers. It is particularly useful for application to bioimplantable substrates such as bone and dental prostheses. The coating can be uniformly applied to substrate surfaces that have complex geometries and surface features, including porous beaded substrates. The thickness range of the coating can vary from about 0.005 to 50 micrometers.

The coating can be effectively and efficiently applied to a variety of substrates. According to the method of the invention, there is first provided an aqueous solution comprising calcium, magnesium, phosphate, and carbonate ions with a pH in the range of about 5–10 and temperature less than about 100° C. Optionally, the solution also includes ions of sodium, potassium, chlorine, sulfate, silicate and mixtures thereof. A suitable substrate is then at least partially immersed in the solution for an amount of time sufficient for the solution to react with the substrate to form a bone mineral ceramic coating and effect the chemical bonding of the coating to the substrate. During the process the solution can be exposed in a controlled environment to an artificial atmosphere having about 0.0001 to 10 mole percent carbon dioxide and a balance of gas or gases selected from the group consisting of oxygen, nitrogen, argon, hydrogen, water steam, ammonia, and mixtures thereof. One particular advantage of the process of the invention is that the coating can be applied at ambient pressures.

DETAILED DESCRIPTION OF THE INVENTION

Figure 1:
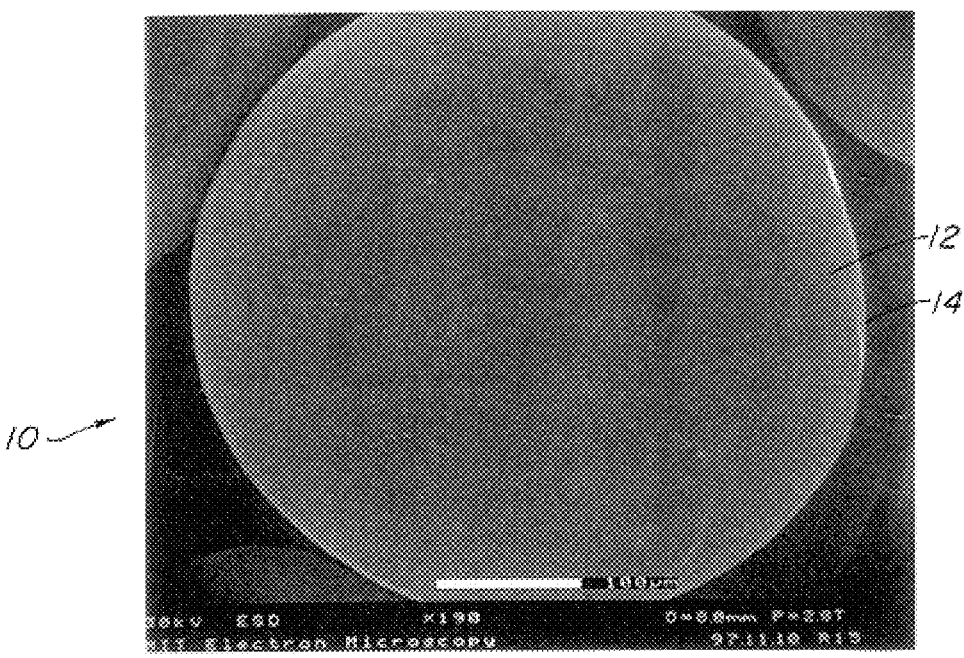
FIG. 1 is a photomicrograph at 190×magnification, showing a coating according to the present invention applied to a Ti6A14V joint prosthesis component bead including Ti6Al4V beads.

The features and other details of the invention will now be more particularly described and pointed out in the claims. It will be understood that the particular embodiments of the invention are shown by way of illustration and not as limitations of the invention. The principal features of this invention can be employed in various embodiments without departing from the scope of the invention.

The invention provides a substantially pure ceramic coating that is chemically bonded to a substrate. The coating is a bioactive, amorphous calcium phosphate that is apatitic and which contains carbonate groups and, optionally, magnesium ions. As used herein, synthetic crystalline bone apatite refers to and includes a calcium phosphate ceramic that is nano-crystalline, having a crystal size of less than about 1 micrometer (less than 100 nanometers, e.g., 50 nm, 20 nm, 5 nm, 1–3 nm).

The coating is particularly useful with bioimplantable substrates such as bone prostheses and dental implants in that the coating can be firmly adhered to the surface of the substrate in a uniform manner, regardless of the surface geometry or surface texture of the substrate. Further, the coating is bone mineral-like in nature, chemically resembling natural bone, so it is able to promote effective and rapid growth of natural bone in and around the substrate so as to firmly affix the substrate in place.

The coating is preferably a bone mineral carbonated nano-crystalline apatite with chemical adsorbed water and having a crystal size less than about 1 micrometer, e.g., less than 100 nanometers (50 nm, 20 nm, 5 nm, 1–3 nm). Ions present in the coating include calcium, magnesium, carbonate, and phosphate. Further, the coating optionally includes sodium, potassium, chlorine, sulfates, silicate and mixtures thereof. The molar ratio of carbonate groups to phosphate groups is generally in the range of about 1:100 to 1:3. The atomic ratio of magnesium to calcium present in the coating is in the range of about 1:100 to 1:10 to 1:4. The atomic ratio of sodium to calcium is generally in the range of about 1:1000 to 1:50 to 1:5. The carbonate content of the synthetic crystalline apatite can be up to about 15% total weight of the apatite. The chemically absorbed/adsorbed water content of the synthetic crystalline apatite can be up to 10 percent by weight of the total weight of the crystalline apatite.

The coating is characterized by an absence of macropores and micropores, and it is similar in composition to bone. The crystal size is less than about 1 micrometer, e.g., less than 100 nanometers, and is so small that ceramic crystals may not be detected by thin-film x-ray diffraction techniques. The small crystal size, and the presence of carbonate groups and magnesium ions contribute to the bone mineral-like nature of the coating. The bone mineral-like properties of the coating also facilitate rapid and effective bone ingrowth.

The coating of the invention is also considered to be dense. The term "dense" as used herein refers to a coating that is substantially free of both micropores and macropores. The term "micropores" refers to pores having a diameter or greater than 100 nanometers. Macropores, generally, have diameters greater than 10 micrometers.

The present invention provides a thin film of a novel synthetic crystalline apatite composition equivalent to or substantially equivalent to bone mineral apatite and methods for growing the composition on medical implants. The composition is a crystalline apatite that, like bone mineral apatite, includes carbonate ($CO_3^{-2}$) ions, magnesium ion, sodium ions, hydrogenophosphate ions and chemically absorbed water with a crystal size generally less than 100 nanometer. The crystalline synthetic apatetic compositions of the present invention are substantially devoid of hydroxyl groups, e.g., the hydroxyl content is below current methods of analytical detection (See for example, FIGS. 13 and 14). The (002) plans of the apatite crystals are oriented to the surface of medical implants.

The method of forming apatite films includes soaking medical implants in an aqueous solution containing calcium ions, phosphate ($HPO_4^{-2}/H_2PO_4^{-1}$) ions, bicarbonate ($HCO_3^{-1}$) ions and magnesium ions at a physiological temperature. Interaction of the bicarbonate ions in the solution with the atmosphere above the film forming solution to establish an equilibrium which raises the pH of the solution. The apatite film is grown onto implants as the pH of the film forming solution rises from about 6.5 to about 7.5, preferably a pH from about 6.85 to about 7.35, facilitating growth of the synthetic apatite. By controlling the $CO_2$ content of the atmosphere above the film forming solution, it has been surprisingly discovered that crystalline apatite can be formed exclusively and that the apatite is not amorphous. In turn, control of the $CO_2$ in atmosphere above the film forming solution also controls the pH of the crystalline apatite forming solution. Establishing an equilibrium between the components in the film forming solution and the atmosphere has proven to be a distinct advantage in forming the synthetic crystalline apatite compositions of the present invention.

Figure 2:
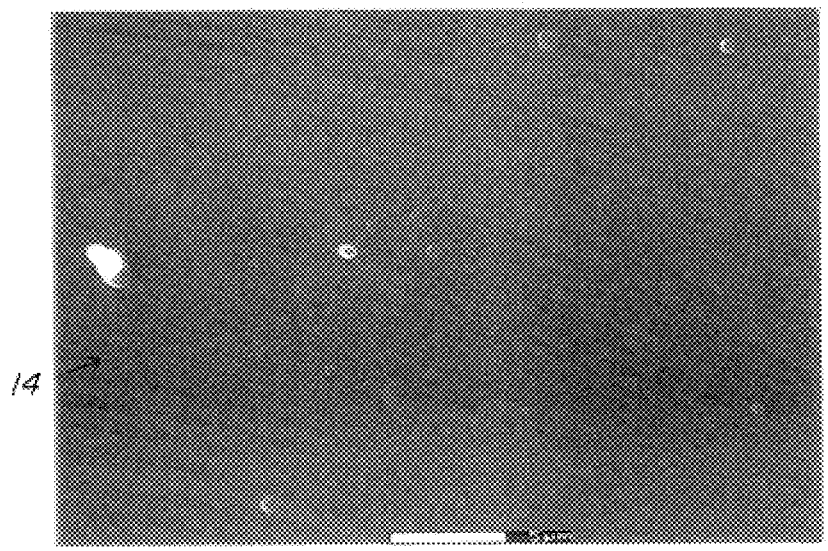
FIG. 2 is a photomicrograph of the coating shown in FIG. 1 at 3000×magnification.
Figure 3:
FIG. 3 is a photomicrograph of the coating shown in FIG. 1 at 10000×magnification.

FIGS. 1–3 illustrate the coating quality and uniformity obtained according to the present invention. The coating shown is that obtained according to Example VIII in Tables 4 and 5. FIG. 1 illustrates a Ti6A4V substrate 10, in the form of a component of a joint prosthesis, having Ti6A4V beads 12 affixed thereto to provide a porous surface texture. The substrate and beads are coated with a bone mineral-like ceramic 14 according to the present invention. FIGS. 1–3 illustrate the smooth and uniform nature of the coating. The amorphous and/or nano-crystalline nature of the coating is also apparent from the photomicrographs of FIGS. 1–3.

Figure 4:
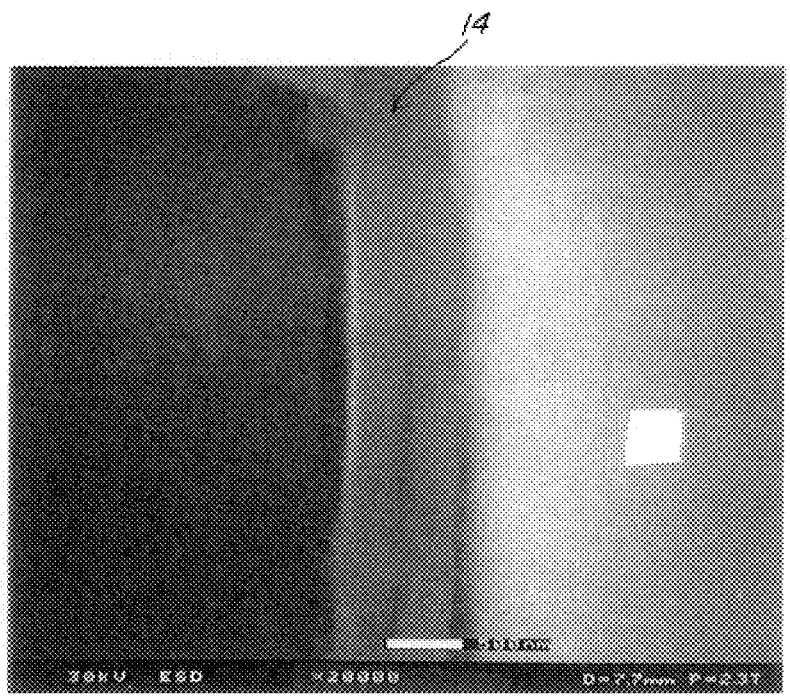
FIG. 4 is a cross-section of a substrate bearing the coating of the present invention.

FIG. 4 is a cross sectional view of a substrate 10 bearing the bone mineral-like coating 14 of the invention. In the illustrated embodiment, the coating is present at a thickness of about 0.7 micrometers.

Figure 5:
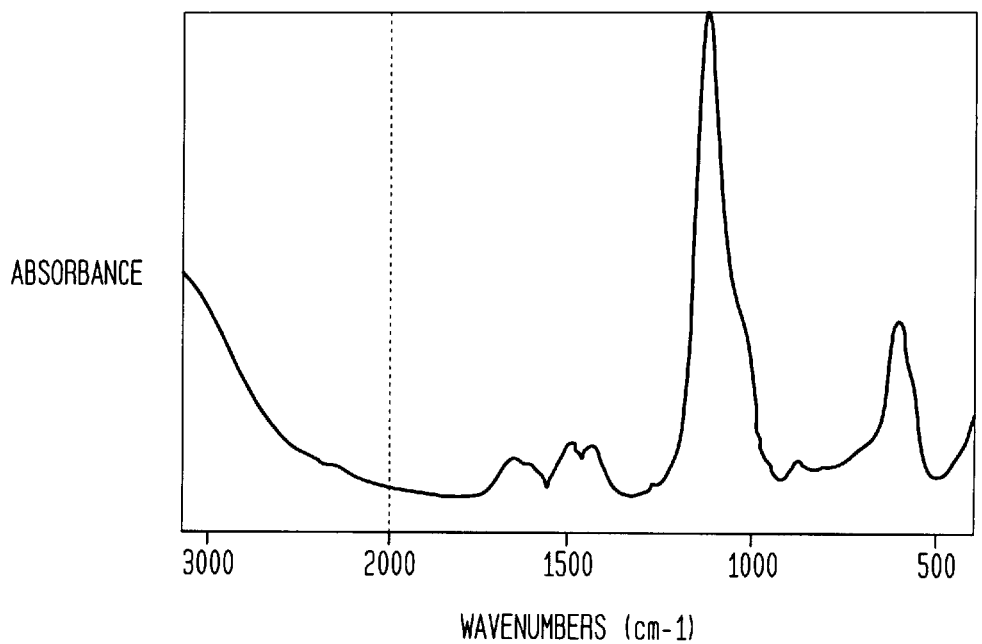
FIG. 5 is a Fourier Transform Infrared (FT-IR) reflectance spectrum obtained for the coating shown in FIG. 4.

FIG. 5 is a FT-IR spectrum of the coating shown in FIG. 4. This confirms that the calcium phosphate within the coating is an amorphous and/or poorly crystallized apatite. The peaks ranging from 1350–1600 $cm^{-1}$ are attributed to carbonate groups, indicating incorporation of carbonate groups into the apatite.

Chemical analysis of the ceramic coating shown in FIG. 5, upon dissolution in 0.002N HCl, established the similarity of the coating to bone mineral. The molar rations of selected functional groups present in this coating is shown in Table 1, below.

TABLE 1

| Molar Ratios | |
|---|---|
| Groups | Ratio |
| $Ca^{2+}/PO^{3-}_4$ | 1.60 |
| $Ca^{2+}/Mg^{2+}$ | 6.31 |
| $(Ca^{2+}/Mg^{2+})/PO^{3-}_4$ | 1.85 |
| $CO^{2-}_3/PO^{3-}_4$ | 0.08–0.25 |

Figure 6:
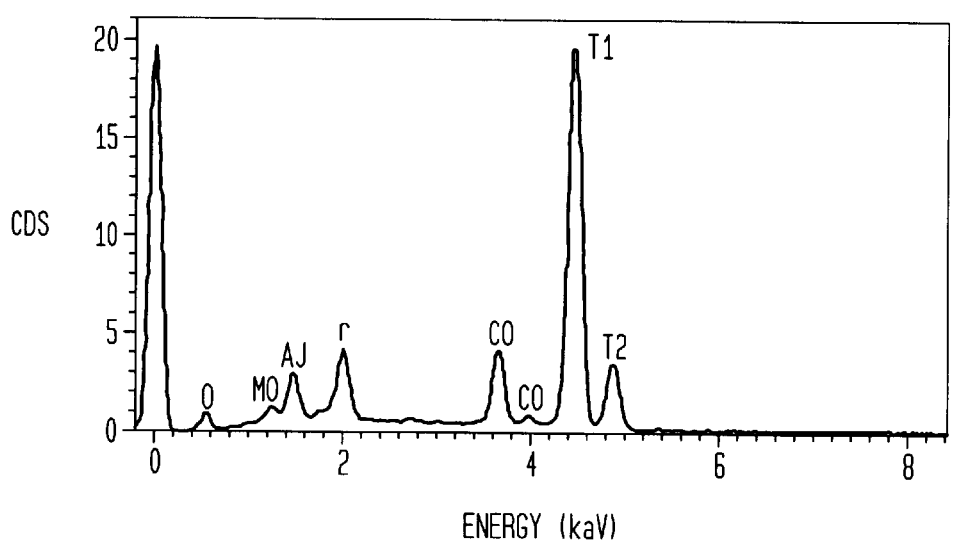
FIG. 6 is a trace obtained by Energy Dispersive X-Ray (EDX) analysis of the coating shown in FIGS. 1–3.

FIG. 6 is an EDX trace of the coating shown in FIGS. 1–3. This trace confirms the presence of calcium phosphate and magnesium in the ceramic coating.

Chemical bonding of the coating to the substrate ensures excellent adhesion of the coating to the substrate. The coating may be applied at virtually any thickness as determined by process parameters explained below. The thickness of the coating is generally in the range of about 0.005 to 50 micrometers, more preferably about 0.1 to 100 micrometers, preferably about 0.5 to 50, and most preferably about 0.2 to 5 micrometers.

The coating of the present invention can be applied to a variety of substrates including silicon, metals, ceramics, and polymers. Exemplary metal substrates include titanium, titanium alloys, cobalt-chromium alloys, tantalum, tantalum alloys, and stainless steel. Polymeric substrates include ultra high molecular weight polyethylene, polyethylene oxide, polylactic acid, polyglycol acid and copolymers of polylactic acid and polyglycol acid.

The substrates to which the coatings are applied can be used in a variety of applications. However, the substrates are particularly well-suited for use with bioimplantable substrates, such as bone prostheses and dental implants. Exemplary bone prostheses include components of artificial joints such as knee, hips, shoulders, and elbows.

The coating of the present invention offers numerous benefits. Because of its chemical similarity to natural bone, the coating possesses high biocompatibility and it is able to encourage rapid bone ingrowth. The coating is also able to be applied in thin, uniform layers. As a result, it can be applied to complex surface geometries such as porous undercut and recessed surfaces. Despite application to such regions, the coating does not alter the surface geometry of the substrate.

The present invention also provides an efficient and effective process for applying a ceramic bone mineral-like coating to a substrate. According to this process, an aqueous solution is provided, having a pH in the range of about 5 to 10, and more preferably about 6.5 to 7.5. The coating contains at least calcium, magnesium, phosphate, and carbonate ions. Optionally, the solution may also contain ions of sodium, potassium, chlorine, sulfates, silicate, and mixtures thereof. The coating process of the invention is conducted at a relatively low temperature, preferably less than 100° C. Coating process are generally conducted in the range of about 20° C. to 60° C., more preferably, from about 35° C. to 55° C.

Typical solution concentrations for calcium range from about 1 to 10 mM, preferably from about 2 to 8 mM. Solution concentrations for phosphate typically range from about 0.5 to about 5 mM, preferably from about 1.0 to about 3 mM. Solution concentration ranges for bicarbonate typically range from about 0.1 to about 27 mM, preferably from about 1 to about 10 mM. Solution concentration ranges for TRIS are typically in a range from about 1 to about 100 mM, preferably from about 8 to about 35 mM. Suitable concentration ranges for hydrochloric acid are from about 1.0 to about 90 mM, preferably from about 8 to about 40 mM. Suitable concentration ranges for magnesium are from about 0.1 to about 8 mM, preferably from about 0.5 to about 5 mM.

Concentrations for additives such as sodium, potassium, chloride, sulfate and silicates can vary appreciably. For example, typical solution concentrations for sodium are from about 100 to about 200 mM. Suitable solution concentrations for potassium range from about 2 to about 8 mM. Suitable solution concentrations for chloride ion range from about 100 to about 250 mM and for sulfate ion, from about 0 to about 1.5 mM. Additional additives include antibiotics which can be incorporated into the apatite film formed on the implant.

The stability of calcium phosphate clusters or colloids is dependant on their hydration and stability. A layer of water on the surface of hydrated colloidal particles prevents contact between the particles, which can result in the formation of aggregates. Additionally, the surface charge on colloidal particles helps to prevent aggregation, since like-charged particles repel each other.

There are generally three ways in which apatitic colloids may acquire a surface charge. One is by chemical reaction at the particle surface involving protons. Ion absorption is believed to be a second way in which apatitic colloids become charged. Labile ions such as $HPO_4^{-2}$, $HCO_3^{-1}$, and $Mg^{+2}$ may attach on the surface of the apatitic colloids by means other than conventional covalent bonding, and can include hydrogen bonding and van der Waals interaction. Ion replacement is a third way in which a colloidal particle may gain a net charge. For example, replacement of $Ca^{+2}$, $PO_4^{-3}$, $OH^{-1}$ (if present) in apatite with $Na^{+1}$, $HPO_4^{-2}$ and $CO_3^{-2}$ can produce a charged surface. All of these chemical reactions, ion absorption and ion replacement are solution chemistry-dependent. Composition, pH and temperature of the solution effect how and when calcium phosphate particles aggregate and grow from the colloidal suspension. Aggregation of apatitic colloids may proceed by coagulation. For example, the reduction of electrostatic repulsion and/or flocculation of labile ions in apatitic colloids disperses the charge-charge repulsions of the individual colloid units to form a large unit. Thus, it has been surprisingly discovered that the pH of supersaturated calcium phosphate-containing apatitic solution is a key factor affecting the growth and aggregation of apatitic colloids and hence the apatite film forming process onto prosthetic surfaces.

When medical implants are soaked in aqueous solutions containing calcium and phosphate ions, phase interactions among the solution, implants and the atmosphere in contact with the solution can cause a change in the solution pH. For example, interaction of bioactive glass ceramic implants with physiological solutions raises the pH of that solution due to the release of sodium and calcium ions from the implants. If aqueous solutions contain, for example, bicarbonate ($HCO_3^{-1}$) ions, interaction of the solution with the atmosphere in contact with that solution can change the pH of the solution. The solution pH may increase due to the interaction, depending on the concentration of bicarbonate ions in the solution and partial pressure of carbon dioxide in the atmosphere above the solution.

For bicarbonate-containing solutions, gas/solution interactions establish the equilibrium of the component:

  (1)

  (2)

  (3)

For example, interaction of the solution and the atmosphere in contact with the solution tends to establish an equilibrium between the $CO_2$ in the solution (S) and the $CO_2$ in the atmosphere. According to Henry's Law, which states that at constant temperature, the solubility of a gas in a liquid is proportional to the partial pressure of that gas in contact with the liquid. Therefore, the partial pressure of $CO_2$ ($P_{CO2}$) in the atmosphere at equilibrium is determined by the following equation when the concentration of $CO_2$ in the solution is [c]:

$$P_{CO2} = kc$$

where k is the Henry's constant of $CO_2$ which is estimated to be $3.38 \times 10^{-2}$ $moL^{-1} \times atm^{-1}$ in water at 25° C.

If the actual partial pressure ($P'_{CO2}$) of $CO_2$ in the atmosphere is less than its partial pressure at equilibrium, then the solution loses $CO_2$ to the atmosphere to increase the partial pressure of $CO_2$. This means that bicarbonate ions are converted to $CO_2$ as described in Eqs (1) and (2). Likewise, the more $OH^{-1}$ groups that are added to the solution, the more $HCO_3^{-1}$ ions convert to $H_2CO_3$ with a release of $CO_2$ into the atmosphere. Therefore, release of $HCO_3^{-1}$ in solution in the form of $CO_2$ results in the increase of pH in the solution.

The degree of supersaturation of a calcium phosphate-containing solution increases as of the pH value of the solution rises. The result is the formation of apatitic colloids. The present invention provides that the apatitic colloids aggregate on the surface of implants which are soaked in the film forming solution, forming an apatite-like calcium phosphate. This is believed to occur due to the reduction of the total surface energy of the implant and/or because of chemical/electrostatic interactions between apatitic colloids and the surface of the implants. As the solution loses $CO_2$ to the atmosphere, the pH of the solution rises until an equilibrium between the $CO_2$ in the solution and the $CO_2$ in the atmosphere is established. The surface charge and composition of the apatitic colloids changes with an increase of pH and decrease of bicarbonate ion concentration. Apatitic colloids can aggregate to form larger units that provide favorable surface conditions for the growth of crystalline apatite in the solution over a pH range from about 6.5 to about 7.5. Consequently, crystalline apatite films form on the surface of the implants in the solution at pH in a range of from about 6.5 to about 7.5. As demonstrated in the examples, formation of crystalline apatite is pH dependent. The resulting thin film formed on implants at a pH above 7.4 (at 45° C.) is amorphous apatitic-like calcium phosphate while films formed in the same solution and at the same temperature but at a pH below 7.3 is a crystalline apatite and is much thicker.

Growth of crystalline apatite helps to decrease the pH of the solution since the apatite crystals require $PO_4^{-3}$ ions. $HPO_4^{-2}$ changes to $PO_4^{-1}$ in the reaction:

$$HPO_4^{-2} = PO_4^{-3} + H^+$$

As such, protons (H+) are released into the solution and thus decrease the pH of the solution as $HPO_4^{-2}$ dissociates into $PO_4^{-3}$ as crystalline apatite is formed on the implant surface. This tends to offset the increase of pH caused by release of $HCO_3^{-1}$ in the solution to the atmosphere.

The degree of pH change in the film forming solution due to the loss of $CO_2$ and the formation of the synthetic crystalline bone apatite can be altered by adding buffering agents such as tris(hydroxymethyl)aminomethane (TRIS) and hydrochloric acid. The concentration of these two buffering components helps to determine the initial pH of the apatite film forming solution and the rate of its pH change due to the deposition of apatite crystals, loss of $CO_2$ and increase of acid. In addition to the concentration of the buffering agents, the partial pressure of $CO_2$ in the atmosphere in contact with the apatite film forming solution, temperature, and the concentration of bicarbonate ions in the solution effect the pH of the solution, and the rate of its change. These factors influence the formation of the synthetic crystalline apatite film on the implant surface. The ratio of the volume of the atmosphere in contact with the solution to the volume of the solution in which medical implants are treated, also effects the pH of the solution and the rate of its change due to the partial pressure of $CO_2$.

The formation of the synthetic crystalline apatite film also depends on the concentration of calcium ions, phosphate ions, magnesium ions as well as the ionic strength of the solution. The ionic strength of the apatite film forming solution can be modulated by the concentration of sodium chloride. Sodium ($Na^+$) ions, magnesium ($Mg^{+2}$) ions, carbonate ($CO_3^{-2}$)ions, hydrogenophosphate ions ($HPO_4^{-2}$) can be incorporated in the apatitic film structure to afford a crystalline apatite substantially equivalent or equivalent to naturally occurring bone mineral apatite. In particular, the kinetic process for forming crystalline apatite which is substantially equivalent to bone mineral, can be modified by changing the initial concentration of magnesium ions. An increase in magnesium ions can delay the growth of crystalline apatite to such an extent that the pH of the solution rises over the critical range before the formation of crystalline apatite starts (Example 5). As a result, only amorphous apatite-like calcium phosphate thin films were formed on the surface of medical implants.

The substrate, or a portion of the substrate, is immersed in the solution for a period of time sufficient to enable the solution to react with the substrate to form the coating thereon. The substrate is usually immersed in the solution for about 1 to 7 days. One of ordinary skill in the art will appreciate, however, that a variety of factors, such as concentration of the major components (e.g., calcium, phosphate, magnesium, and hydrocarbonate), pH, and the environment in contact with the solution, will affect the process duration. Generally, the coating thickness increases with immersion time. It is believed that the substrate surface is converted into the calcium phosphate coating material as a result of the immersion within the solution.

A suitable solution is prepared by adding to deionized water the necessary components to obtain the desired ions upon dissociation. In one embodiment, as noted above, the solution need only contain calcium ions, magnesium ions, phosphate ions, and carbonate ions in the concentration range noted below in Table 2. Optionally, sodium, potassium, chlorine, sulfate, and silicate ions may be present in the solution at the concentration range noted in Table 2. Tris(hydroxymethyl)aminomethane may be added to the solution at a concentration range from about 1 to 100 mM to control pH. In addition, hydrogen peroxide may be added at 1–50 mM to facilitate chemical bonding between the substrate and the coating. Tables 2 and 3 illustrate exemplary constituents of the solution and exemplary compounds that can be added to the solution to obtain the desired ions.

TABLE 2

Exemplary Constituents

| Ion | mM |
| --- | --- |
| Na+ | 130–200 |
| K+ | 3.5–7 |
| $Mg^{2+}$ | 0.7–2 |
| $Ca^{2+}$ | 2–4 |
| $Cl^-$ | 96–250 |
| $HCO^{3-}$ | 5–50 |
| $SO_4^{2-}$ | 0–1 |
| $HPO_4^{2-}$ | 1–2.5 |

TABLE 3

Exemplary Solution-forming Compounds

| NaCl |
| --- |
| KCl |
| $K_2HPO_4.3(H_2O)$ |
| $MgCl_2.6(H_2O)$ |
| HCl |
| $CaCl_2$ |
| $Na_2SO_4$ |
| $NaHCO_3$ |

In one embodiment the solution is exposed to a controlled environment which includes an artificial atmosphere containing about 0.0001 to 10 mole percent carbon dioxide, and more preferably less than about 3 mole percent carbon dioxide. The balance of the atmosphere may include oxygen, nitrogen, argon, hydrogen, water steam, ammonia, and mixtures thereof. The artificial atmosphere can be passed over the solution at a flow rate ranging from 0 to about 10 liters per minute for every liter of solution.

The interaction among the artificial atmosphere, the solution, and the substrate leads to the conversion of the implant surface to a bone mineral-like ceramic. This coating is formed on all surfaces of the substrate that are exposed to the solution, including those that are recessed, undercut, flat, concave, convex or of any other desired shape or orientation. Further, the solution is able to penetrate small pores and voids in the surface in the material so as to form a coating on a substrate of virtually any surface geometry or surface texture. Thus, the coating can be formed on implants with complicated geometrical features, including beaded substrates which have a porous surface such as those designed for biological fixation. A particular advantage of the process of the invention is that the surfaces of such substrates, particularly those present on biological implants, are expected to stimulate bone ingrowth and to increase bone apposition. Thus, the process provides an effective technique to combine a bone mineral-like ceramic with a porous surface so that a quick and strong fixation can be achieved with the implants. The adhesion strength of the coating to a polished substrate is believed to be in excess of 30 MPa.

Figure 7:
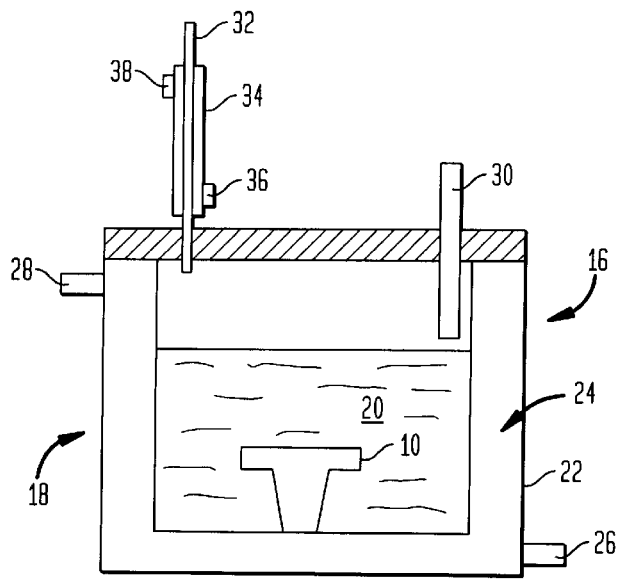
FIG. 7 is schematic view of a reactor vessel suitable to effect the process of the invention.

FIG. 7 illustrates a reactor vessel system 16 that is useful to effect the process of the invention. The reactor vessel includes a chamber 18 for containing an aqueous solution 20. Preferably, the chamber 18 is defined by a double walled structure 22 that includes an internal space 24 for accommodating a circulating fluid such as water. In one embodiment, the cooling fluid may be circulated at a temperature of about 37° C. The reactor vessel 16 includes a cooling fluid input port 26 and a cooling fluid output port 28. The reactor vessel 16 also includes a gas inlet port 30 for directing an artificial atmosphere into the reactor vessel and into contact with the aqueous solution. A gas outlet port 32 is also present to vent gas from within the vessel. In the illustrated embodiment, the gas outlet port 32 is surrounded by a cooling jacket 34 with coolant inlet and outlet ports 36, 38 to cool the exiting gas. In one embodiment cold water (e.g., at about 2° C.) is circulated through the cooling jacket.

As noted above, the composition of the aqueous solution can vary within certain limits. Table 4 provides examples of various suitable compositions of the aqueous solution.

TABLE 4

Composition of the Aqueous Solution

| (mM) | Na+ | K+ | $Mg^{2+}$ | $Ca^{2+}$ | Cl− | $HPO_4^{2-}$ | $HCO_3^{-1}$ | $SO_4^{2-}$ | tris* | pH/37° C. |
|---|---|---|---|---|---|---|---|---|---|---|
| Example I | 178.7 | 6.24 | 1.88 | 2.81 | 202.5 | 1.74 | 27.0 | 0.63 | 50 | 7.15 |
| Example II | 178.6 | 6.29 | 1.88 | 2.66 | 201.4 | 1.66 | 27.0 | 0.63 | 50 | 7.40 |
| Example III | 178.7 | 6.24 | 1.88 | 2.81 | 202.5 | 1.74 | 27.0 | 0.63 | 50 | 7.15 |
| Example IV | 178.7 | 6.24 | 1.88 | 2.81 | 202.5 | 1.74 | 27.0 | 0.63 | 50 | 7.15 |
| Example V | 178.6 | 6.25 | 1.88 | 2.80 | 202.5 | 1.75 | 27.0 | 0.63 | 50 | 7.25 |
| Example VI | 178.6 | 6.25 | 1.88 | 2.80 | 202.5 | 1.75 | 27.0 | 0.63 | 50 | 7.25 |
| Example VII | 178.6 | 6.25 | 1.88 | 2.80 | 202.5 | 1.75 | 27.0 | 0.63 | 50 | 7.25 |
| Example VIII | 178.6 | 6.25 | 1.88 | 2.80 | 202.5 | 1.75 | 27.0 | 0.63 | 50 | 7.25 |

*tris(hydroxymethyl)aminomethane

Table 5 illustrates various parameters of the coating process, as well as a variety of substrates able to be coated according to the process of the present invention.

TABLE 5

Substrates and Parameters of the Process.

| | Substrate | a.a.*($CO_2 + O_2$) mol % $CO_2$ | Flow Rate (l.p.m.) | Temperature (° C.) solution outlet | | Time (day) |
|---|---|---|---|---|---|---|
| Example I | c.p.Ti disk** | 1.0 | 5.0 | 37.0 | 4.0 | 2 |
| Example II | CoCr disk | 0.0 | 5.0 | 37.0 | 4.0 | 2 |
| Example III | S-ROM sleeve | 1.0 | 2.5 | 37.0 | 4.0 | 3 |
| Example IV | S-ROM cup | 1.0 | 0.0 | 37.0 | 4.0 | 3 |
| Example V | knee femoral comp. | 1.0 | 2.0 | 37.0 | 2.0 | 2 |
| Example VI | knee tibia comp. | 1.0 | 0.0 | 37.0 | 2.0 | 4 |
| Example VII | Ti6A14V disk | 0.0 | 0.5 | 37.0 | 2.0 | 4 |
| Example VIII | Ti6A14V disk | 1.0 | 0.5 | 37.0 | 2.0 | 4 |

*a.a. = artificial atmosphere
**c.p. = commercially pure

The following examples serve to further describe the invention.

EXAMPLE 1

Ten pieces of Ti6A4V disks (about 16 mm in diameter and 3 mm thick) were sandblasted. Ten Ti6A4V disks of the same size were polished. All disks were first cleaned in detergent, followed by ultrasonic cleaning in acetone, followed by an ethanol wash, and finally rinsed extensively with de-ionized water and dried at 60° C. overnight. The synthetic bone mineral source solution (apatite film forming solution) was prepared by dissolving 17.5744 g of NaCl, 0.4106 g of KCl, 1.0955 g of $K_2HPO_4/3 H_2O$), 1.2201 g of $MgCl_2/6H_2O$, 37 ml of 1N HCl, 1.3335 g of $CaCl_2$, 0.1774 g of $Na_2SO_4$, 4.2410 g of TRIS and 1.3287 g of $NaHCO_3$ in about 1700 ml of de-ionized water and then diluted to make 2 liters of solution. The initial pH of the solution was 6.671 at 43.3° C. and the composition of the as-prepared solution was:

[Ca]=6.0 mM, [P]=2.4 mM, [$HCO_3^{-1}$]=8 mM, [Mg]=3 mM, [TRIS]=17.5 mM, [HCL]=18.5 mM.

Figure 8:
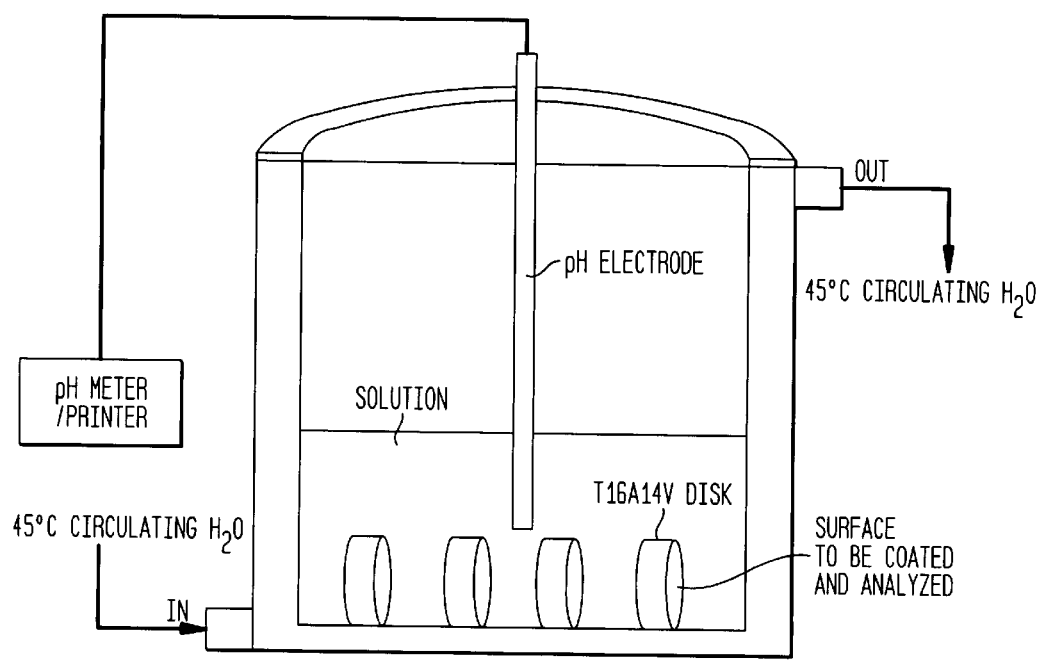
FIG. 8 is a schematic view of a reactor vessel suitable for growing synthetic osteoapatite (synthetic bone-mineral) thin film of the surface of titanium.

The as-prepared solution was clean and free of any visible precipitate. 300 ml of the fresh solution was taken and loaded in a jacked glass reactor and twenty Ti6A4V disks were soaked in the solution, as shown in FIG. 8. A pH electrode was placed near the disks to monitor the change of pH over time. The reactor was sealed. The total volume of the available space in the reactor was about 1.8 liters with 300 ml taken by the solution. Thus, the ratio of the volume of atmosphere in contact with the solution to the volume of that solution was about 5. A circulating water bath was connected with the jacked reactor to maintain the reaction temperature at 45° C. The reaction proceeded at 45° C. for about 64 hours. All titanium disks were then rinsed extensively with de-ionized water and dried at 60° C. overnight. The samples were then analyzed with Fourier Transform Infrared Spectroscopy (FTIR), X-ray Diffractometer (XRD), Scanning Electron Microscopy (SEM) linked with Energy Dispersive Spectroscopy (EDS). The results are shown in FIGS. 8 through 13.

Figure 9:
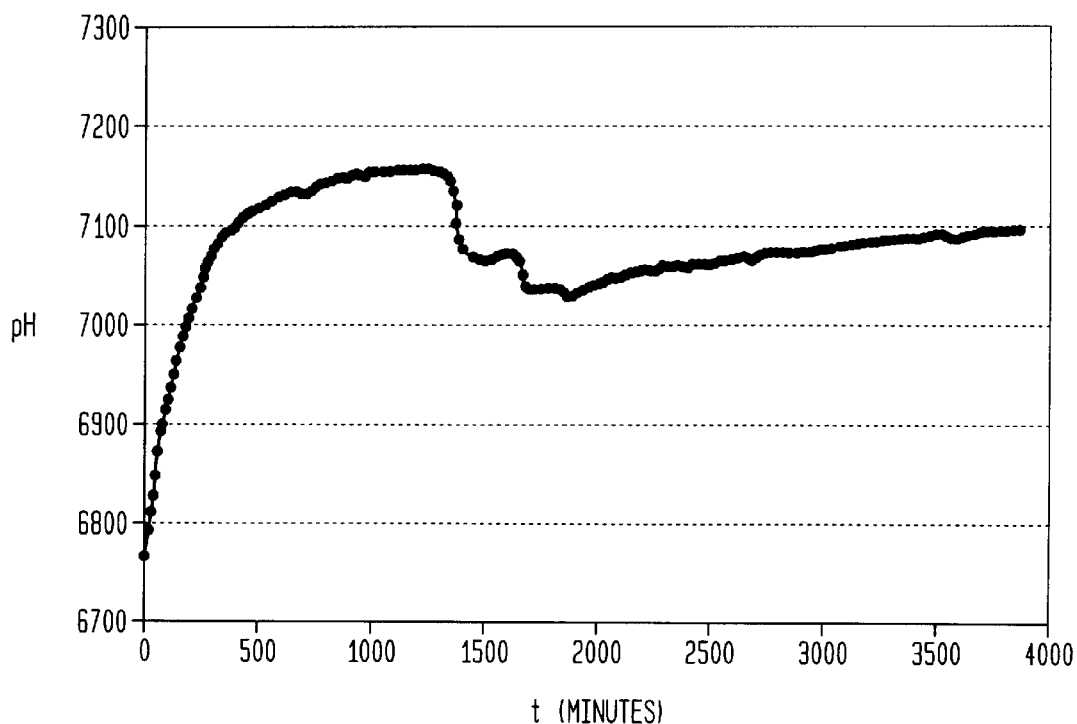
FIG. 9 depicts the change of the pH in the solution of Example 1 with the soaking time.

FIG. 9 demonstrates that the pH of the solution first increases due to the liberation of $HCO_3^{-1}$ in the solution to the atmosphere in the form $CO_2$. The drop of pH results from the formation synthetic bone mineral film that accompanies the reaction: $HPO_4^{-2} = PO_4^{-3} + H^+$.

Figure 11:
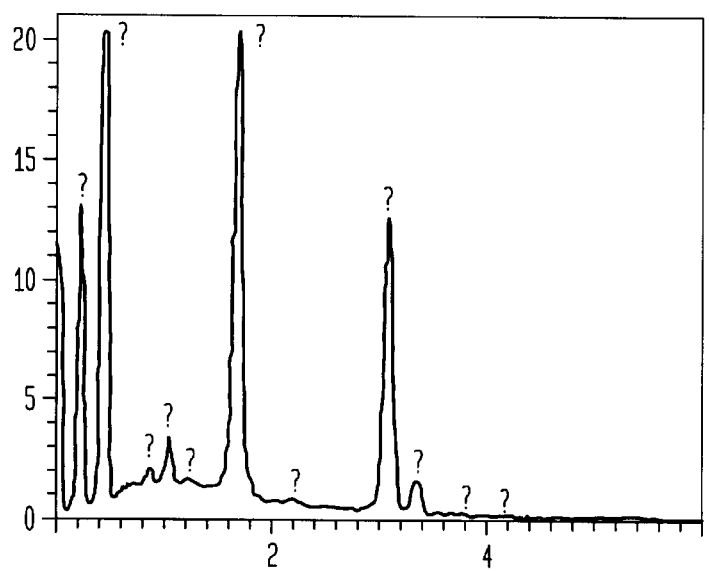
FIG. 11 are EDS results for the synthetic bone mineral containing magnesium and sodium grown on the sandblasted Ti6A4V discs of Example 1.
Figure 10A:
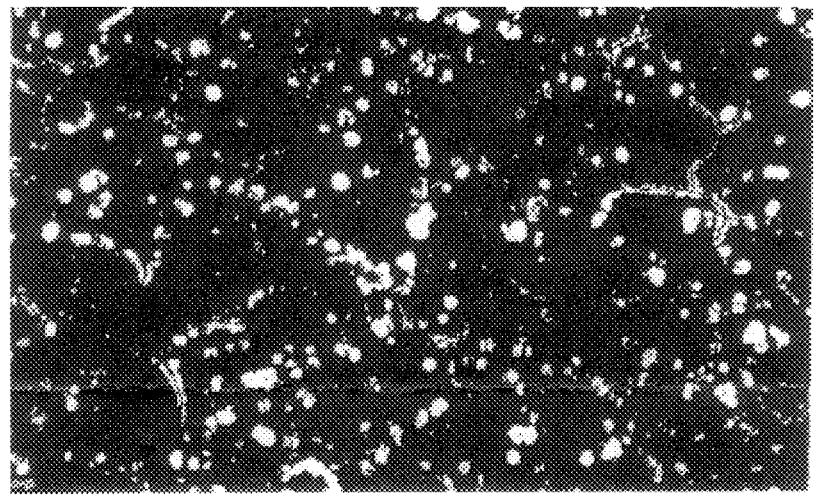
FIGS. 10 A, B and C are SEM pictures for a synthetic bone mineral film grown on sandblasted surfaces of Ti6A4V discs of Example 1.
Figure 10B:
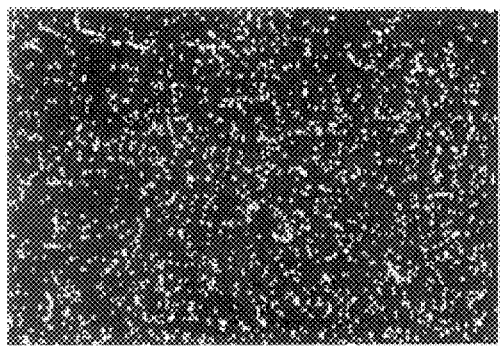
Figure 10C:
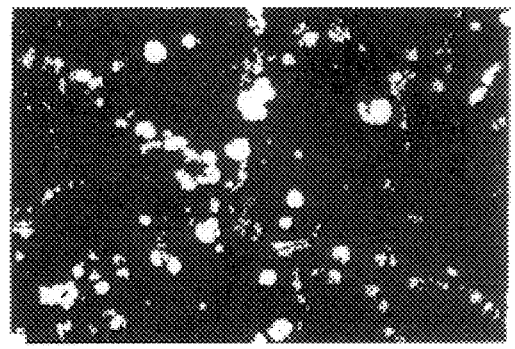
Figure 12:
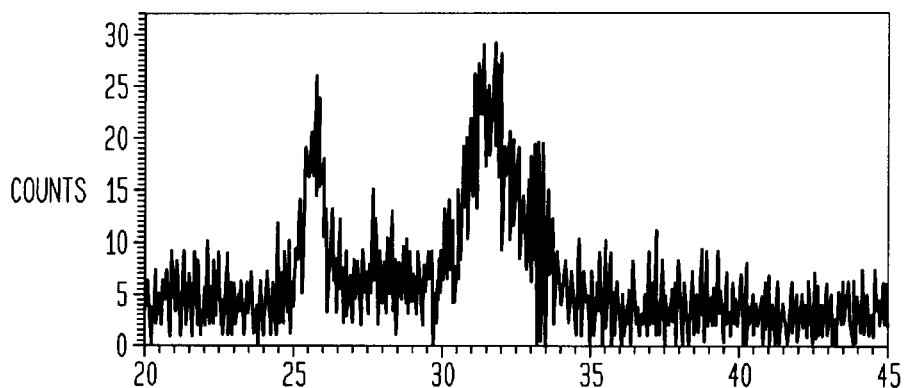
FIG. 12 depicts a thin film XRD pattern of the synthetic bone mineral (pure apatite) grown on the surface of sandblasted Ti6A4V discs of Example 1.

FIGS. 10 through 12 are SEM's, EDS results and XRD patterns of the crystalline synthetic apatite films formed on the surface of Ti6A4V. The pure apatite contains magnesium and sodium.

Figure 13:
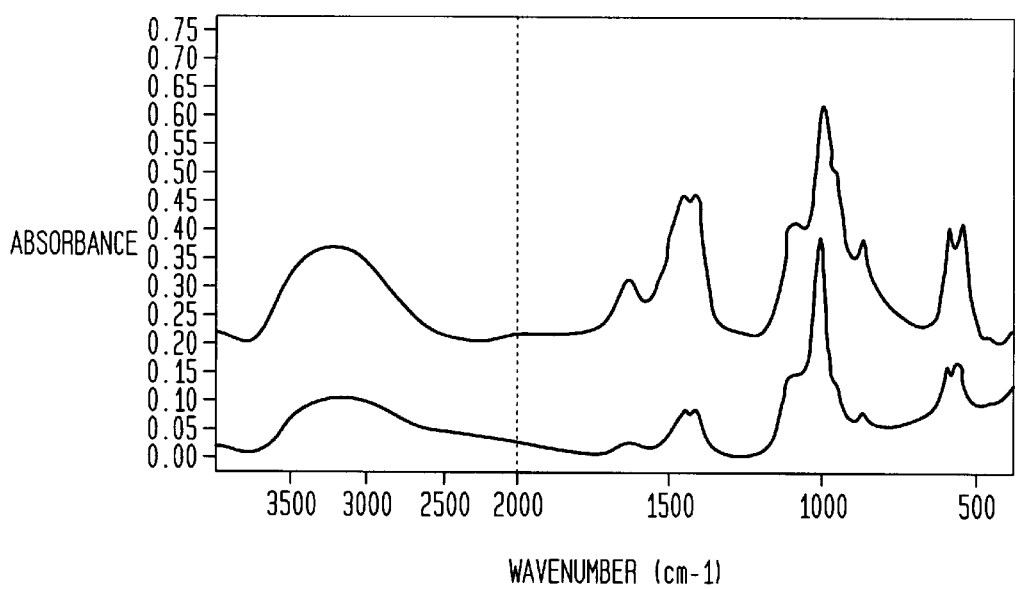
FIG. 13 depicts FTIR spectra of the synthetic bone mineral formed on the sandblasted surface (top) and the polished surface of Ti6A4V discs from Example 1.

FIG. 13 includes FTIR spectra of the synthetic bone mineral formed on the sandblasted surface (top) and the polished surface of Ti6A4V discs showing that the crystalline apatite contains carbonate ($CO_3^{-2}$) groups, hydrogenophosphate ($HPO_4^{-2}$) ions and absorbed water.

EXAMPLE 2

Figure 14:
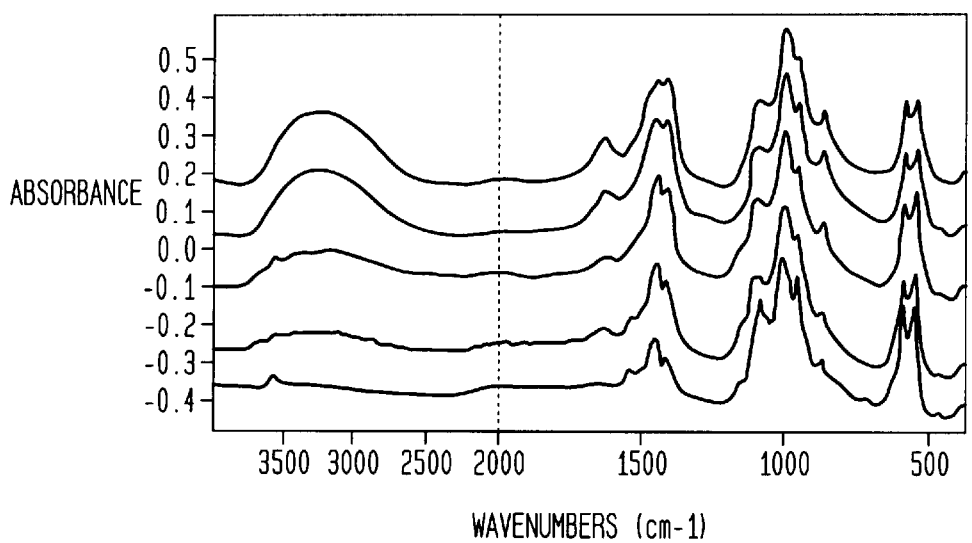
FIG. 14 depicts FTIR spectra of the synthetic bone mineral film, prepared as in Example 1, after heating at different temperatures (from top to bottom: room temperature, 120, 450, 550 and 650° C.).

The synthetic bone apatite mineral film formed on the sand-blasted surface of the Ti6A4V disks, prepared as in Example 1, was heated at 120, 200, 300, 400, 450, 500, 550, 600, 650° C. and then analyzed by FTIR. The FTIR patterns of FIG. 14 show that bands around 1600 $cm_{-1}$, and broad bands around 3200 $cm^{-1}$, which are assigned to $H_2O$, do not disappear until after heating at 650° C. This indicated that synthetic apatite bone mineral contains chemically absorbed water in its structure and not hydroxyl ions.

EXAMPLE 3

Twelve Ti6A4V disks each about 15.6 mm in diameter and 3 mm thick and twelve Ti6A4V each about 31.25 mm in diameter and 3 mm thick were sandblasted. The discs were soaked in 450 ml of the solution used in Example 1 and the process of Example 1 was repeated two times to grow a thicker synthetic bone mineral film. Six 31.25 diameter mm disks with the synthetic bone mineral film were used to determine the chemical composition of the mineral. All the disks were dried at 120° C. overnight. Each of these six disks was soaked in 50 ml of 0.2N HCl to dissolve the mineral film. The solution was then analyzed by means of atomic absorption spectrometer to measure the concentration of Ca, Mg, Na and by photo-spectrometer to measure the phosphate concentration.

Composition of the Synthetic Bone Mineral

Ca/P=1.48

Ca/Mg=19.06; Ca/Na=23.83

(Ca+Mg+Na)/P=1.62

Two 31.25 diameter mm disks with the synthetic bone mineral film and another two 31.25 diameter mm disks with the synthetic bone mineral film were dried at 120° C. for 1 hrs. After the samples were cooled to the room temperature, each disk was weighed. Three disks were fired at 400° C. for 60 minutes in a vacuum furnace and another three were fired at 925° C. for 60 minutes. They were weighed again to determine the weight loss. Thereafter, the disks were soaked in 50 ml of 0.2 N HCl to dissolve the synthetic mineral film. The disks were then rinsed extensively with de-ionized water, dried at 120° C. for 60 minutes. Finally, the discs were weighed again to determine the total mass of the mineral film on the titanium.

Results

Weight loss (the loss of the chemically absorbed water) was between about 1.6–2.5 wt % after heating at 400° C.

Weight loss (the loss of the chemically absorbed water+ $CO_2$) was about 8–10 wt % after heating at 925° C.

Consequently, in aspect of the invention, the final crystalline apatite forms coating on the medial implant which is subjected to a further treatment at a temperature of less than 1000° C.

EXAMPLE 4

This experiment demonstrated that the growth of crystalline synthetic bone mineral occurred preferably over a pH range of pH 6.7–pH 7.3 at 45° C.

The synthetic bone mineral referred to as osteoapatite film forming solution was prepared by dissolving 17.5743 g of NaCl, 0.4097 g of KCl, 1.0953 g of $K_2HPO_4.3H_2O$, 1.2193 g of $MgCl_2.6H_2O$, 37 ml of 1N HCl, 1.0006 g of $CaCl_2$, 0.1779 g of $Na_2SO_4$, 4.2397 g of TRIS and 1.3279 g of $NaHCO_3$ in about 1500 ml of de-ionized water and was then diluted to make 2 litters of the solution. The initial pH of the solution was recorded at 6.666 at 43.9° C. The approximate composition of the as-prepared solution was:

[Ca]=6.0 mM, [P]=2.4 mM, [$HCO_3$]=8 mM, [Mg]=3.0 mM, [TRIS]=17.5 mM, [HCl]=18.5 mM.

The as-prepared solution was clean and free of any visible precipitate. 300 ml of the fresh solution was added in jacketed glass reactor 1 while another 300 ml of the fresh solution was added in jacketed glass reactor 2 (total volume of each reactor being about 1800 ml). Eight polished titanium disks about 16.5 mM in diameter (2 mm thick) were soaked in each of the reactors. One pH electrode was inserted near the disks in each reactor to monitor the change of pH value over time. Reactor 2 was fully sealed while reactor 1 had a hole in the top cover to provide access to free atmosphere. A cooling condenser whose temperature was set at 2° C. was placed above the hole to reduce evaporation of $H_2O$ that could cause the change of the concentration of solution. The reaction in reactor 1 proceeded at 45° C. for 5470 minutes while the reaction in reactor 2 proceeded at 45° C. for 4290 minutes. All disks were then rinsed extensively with de-ionized water and dried at 60° C. overnight. The specimens were analyzed with XRD and FTIR.

Figure 15A:
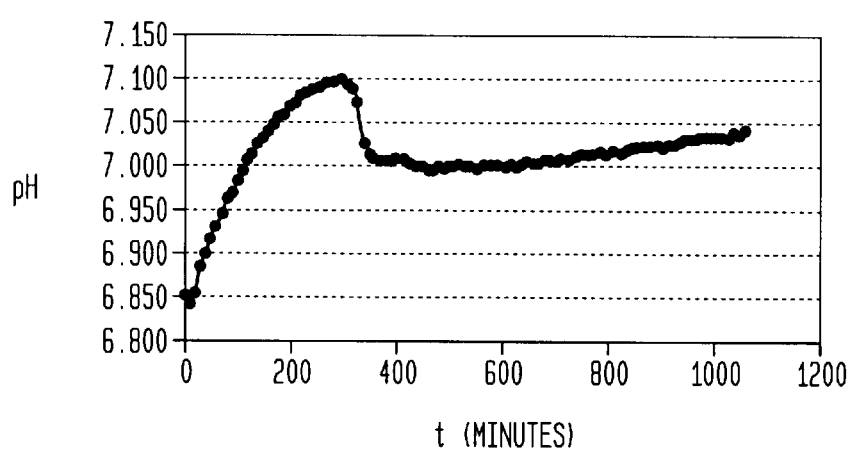
FIGS. 15A and 15B depict the change of pH in the solutions in Example 4 with reactor 1 (A, top) and reactor 2 (B, bottom) in view of the soaking time.
Figure 15B:
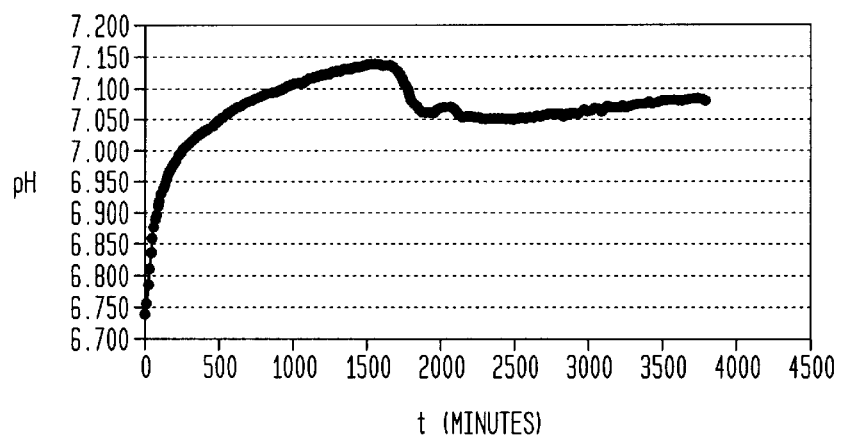

The change of pH in the solutions in the two reactors are shown in FIG. 15A and FIG. 15B. FIGS. 15A and 15B show the change of pH in the solutions in reactor 1 (A, top) and reactor 2 (B, bottom) with the soaking time. Note that the pH in the reactor 1 kept rising and stabilized at 7.4 at 45° C. No drop of pH was observed. The pH of the solution in reactor 2 kept rising until a pH 7.235 and then dropped.

Figure 16:
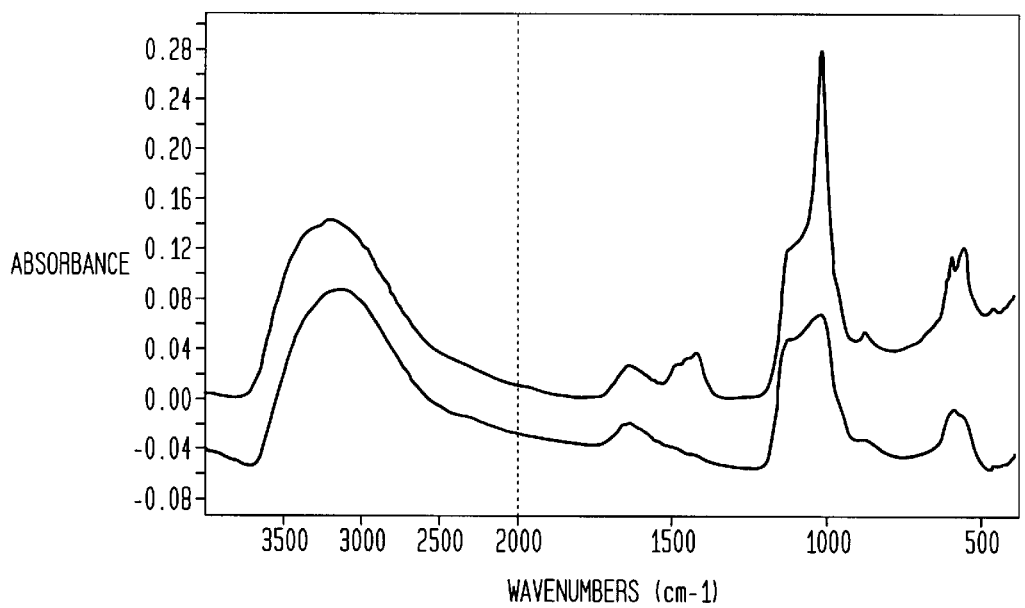
FIG. 16 depicts two FTIR spectra for the surfaces of the titanium disk soaked in reactor 2 (top) and in the reactor 1 (bottom) in Example 4.

Apparently, because of the open hole, $CO_2$ could not accumulate in atmosphere in contact with the solution and the solution continued to loss $CO_2$ until depletion. Because reactor 2 was sealed, $CO_2$ liberated from the solution accumulated in the atmosphere above the solution and thus the rate of removal of $CO_2$ from the solution was decreased. XRD results showed that the film formed on the titanium disks in reactor 1 was amorphous apatite-like calcium phosphate while the film formed on the titanium in reactor 2 was crystalline apatite. The results are consistent with FTIR analysis. As shown in FIG. 16, the calcium phosphate film formed on the titanium soaked in reactor 2 was crystalline carbonated apatite while the calcium phosphate film formed on the titanium soaked in reactor 1 was amorphous.

EXAMPLE 5

This experiment demonstrated the effect of magnesium ion on the growth of crystalline synthetic bone mineral film.

A series of solution with different concentration of magnesium ions were tested to determine when crystalline synthetic bone mineral begins to form and how fast the growth of the mineral film occurred.

The concentrations of magnesium ions tested in this experiment are as follows:

1.8 mM; 1.95 mM; 2.4 mM; 2.5 mM, 3.0 mM; 3.25 mM and 3.5 mM.

Figure 17A:
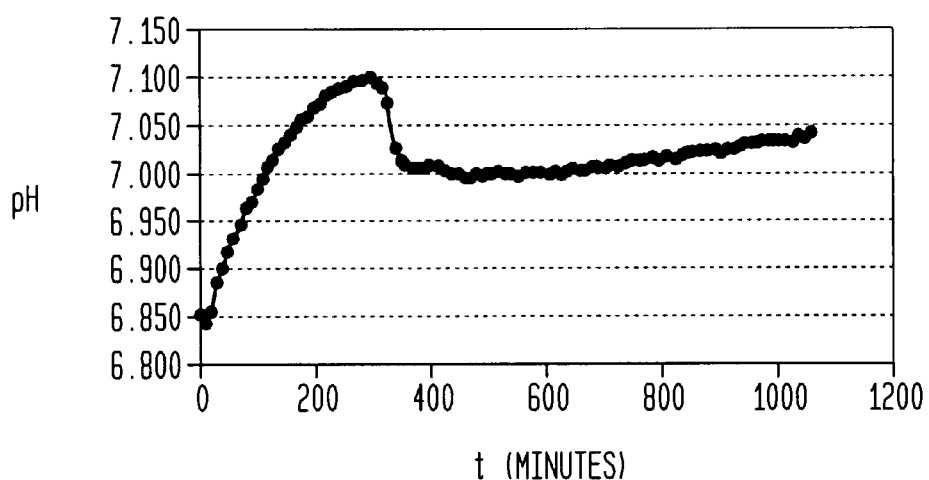
FIGS. 17A and B show the change of pH of the solution with the soak time at the magnesium concentrations of 1.8 mM (top) and 3.5 mM (bottom).
Figure 17B:
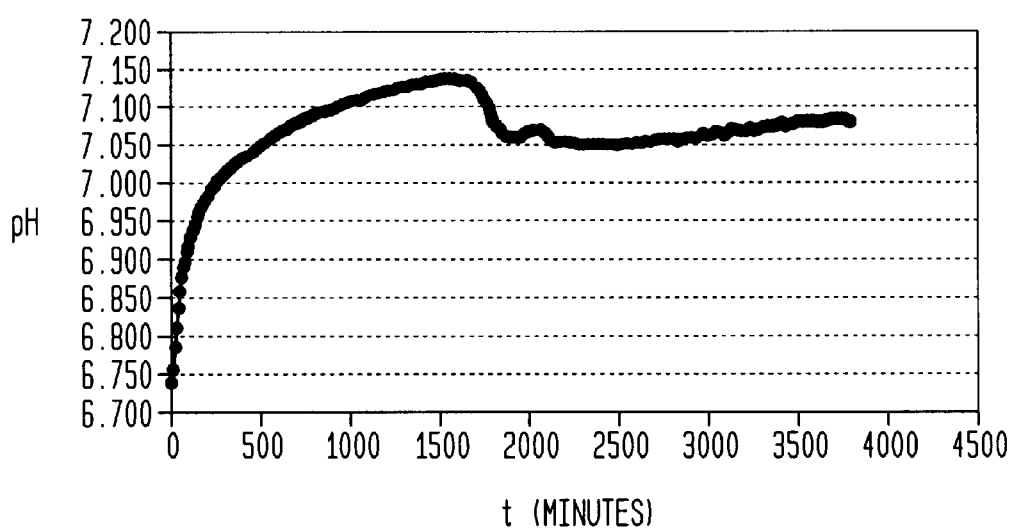

The concentrations of calcium, phosphate and other elements are the same as in the solution described in Example 6. 300 ml of the fresh solution was added to a jacketed glass reactor. The reaction proceeded as described in Experiment 1. It was found that the time when the osteoapatite film began to grow on the surface of titanium and the rate of its growth varied, depending upon the concentration of magnesium ions. As shown in FIGS. 17A and B, the osteoapatite started to grow about 300 minutes after reaction at the magnesium concentration of 1.8 mM while this time increased to about 1600 minutes if the magnesium concentration was increased to 3.5 mM.

EXAMPLE 6

This experiment demonstrated the growth of a crystalline synthetic bone mineral film on acetabula cup with a bead-coated porous surface.

The osteoapatite film forming solution was prepared by dissolving 17.5721 g of NaCl, 0.4124 g of KCl, 1.0986 g of $K_2HPO_4 \cdot 3H_2O$, 0.7938 g of $MgCl_2 \cdot 6 H_2O$, 37 ml of 1N HCl, 1.3319 g of $CaCl_2$, 0.1800 g of $Na_2SO_4$, 4.2411 g of TRIS and 1.0902 g of $NaHCO_3$ in about 1500 ml of de-ionized water and was then diluted to make 2 liters of the solution. The initial pH of the solution was recorded at 6.74 at 36.9° C. and the approximate composition of the as-prepared solution was:

[Ca]=6.0 mM, [P]=2.4 mM, $[HCO_3]$=6.5 mM, [Mg]=1.8 mM, [TRIS]=17.5 mM, [HCl]=18.5 mM.

The as-prepared solution was clean and free of any visible precipitate. 150 ml of the fresh solution was taken and loaded in a plastic bottle and three polished titanium disks (16.5 mm in diameter and 2 mm thick) and one titanium acetabula cup with a titanium bead-coated porous surface (JJPI) were soaked in the solution. The bottle containing the solution and the implant was placed in an incubate at 37° C. The reaction proceeded at 37° C. for about 10 hours. The disk and the cup were then rinsed extensively with de-ionized water and dried at 60° C. overnight. The disks were analyzed by Fourier Transform Infrared Spectroscopy (FTIR) and the results showed the formation of osteoapatite film on the surface of the titanium disks. The acetabula cup was examined with Scanning Electron Microscopy (SEM) linked with Energy Dispersive Spectroscopy (EDS). The results are demonstrated that the titanium beads sintered on the titanium cup were fully coated with the osteoapatite film. The thickness of the film was about 2–3 micrometers.

Although the present invention is described with respect to particular embodiments and features and uses, numerous variations or equivalents are possible without departing from the spirit or scope of the claimed invention. All references cited herein are expressly incorporated by reference in their entirety, including those in the background section.

What is claimed is:

1. A process for forming a synthetic crystalline apatite coating on a substrate, comprising the steps of:
   providing a substrate;
   providing an aqueous solution comprising calcium ions, phosphate ions, and carbonate ions having an initial pH level in the range of 6.0 to 7.5 and a temperature less than or equal to 100° C.; and
   immersing at least a portion of the substrate in the aqueous solution for an amount of time sufficient to form a synthetic crystalline apatite ceramic coating and effect the chemical bonding of the coating to the substrate, while the aqueous solution maintains a pH level below 8.0.

2. The process of claim 1 wherein the aqueous solution is exposed in a controlled environment where sufficient carbon dioxide is maintained in the atmosphere above the aqueous immersion solution, such that the pH of the solution is maintained at or below 7.5.

3. The process of claim 1 wherein the calcium ions are present at a concentration in the range of about 1–10 mM, the magnesium ions are present at about 0.1–8 mM, the phosphate ions are present at a concentration in the range of about 0.50–5 mM, and the carbonate ions are present in the range of about 1–50 mM.

4. The process of claim 1 wherein the aqueous solution further comprises ions selected from the group consisting of sodium, potassium, magnesium, chlorine, sulfate, silicate and mixtures thereof.

5. The process of claim 4 wherein the sodium ions are present at about 100–200 mM, the potassium ions are present at 2–8 mM, the chlorine ions are present at about 100–250 mM, and the sulfate ions are present at 0–1.5 mM.

6. The process of claim 1, wherein the synthetic crystalline apatite ceramic coating has a thickness in the range of about 0.005–50 µm.

7. The process of claim 1, wherein the substrate is selected from the group consisting of metals, ceramics, silicon, and polymers.

8. The process of claim 1 wherein the apatite ceramic is a dense coating, having a crystal size less than about 1 µm.

9. The process of claim 1, wherein a surface texture of the substrate and a surface geometry of the substrate are preserved.

10. The process of claim 1 wherein the apatite ceramic coating includes a carbonated crystalline apatite that is substantially devoid of hydroxyl groups in its crystal structure, the carbonated crystalline apatite containing chemically adsorbed water.

11. The process of claim 1 wherein the pH of the aqueous solution is in the range of about 6.7 to 7.4 and the temperature of the aqueous solution is in the range of about 30° C. to 50° C.

12. A process for growing a synthetic bone mineral carbonated crystalline apatite coating on a substrate, comprising the steps of:
    providing a substrate;
    preparing an aqueous solution comprising calcium ions, phosphate ions, carbonate ions and magnesium ions, the aqueous solution being transparent and having an initial pH level in the range of about 6.0 to 7.5 and a temperature in the range of about 20° C. to 60° C.; and
    contacting the substrate with the aqueous solution by soaking at least a portion of the substrate in the aqueous solution and allowing the aqueous solution to react with the substrate, wherein the initial pH level of the aqueous solution increases to an increased pH level less than pH 8.0 as the aqueous solution begins to react with the substrate and the increased pH level decreases as a film of synthetic carbonated crystalline apatite coating begins to grow on at least the portion of the substrate in contact with the aqueous solution to yield a synthetic carbonated crystalline apatite coating formed on the substrate that is substantially devoid of hydroxyl groups, includes chemically adsorbed water, and is chemically bonded to at least a portion of the substrate.

13. The process of claim 12, wherein the aqueous solution further comprises a buffering component selected from the group consisting of tris(hydroxymethyl)aminomethane, hydrochloric acid, and combinations thereof, the buffering component being effective to maintain the pH level of the aqueous solution at or below 7.5 and to control a rate at which the pH level of the aqueous solution changes as the aqueous solution reacts with the substrate.

14. The process of claim 13, wherein the tris(hydroxymethyl)aminomethane is present in the aqueous solution at a concentration in the range of about 5–100 mM and the hydrochloric acid is present in the aqueous solution at a concentration in the range of about 5–90 mM.

* * * * *